United States Patent
Ma et al.

(10) Patent No.: US 11,067,492 B2
(45) Date of Patent: Jul. 20, 2021

(54) PHYSICAL SIMULATION AND CALIBRATION DEVICE AND METHOD FOR FORMATION PRESSURE TESTING

(71) Applicant: SouthWest Petroleum University, Sichuan (CN)

(72) Inventors: Tianshou Ma, Sichuan (CN); Nian Peng, Sichuan (CN); Ping Chen, Sichuan (CN); Xingming Wang, Sichuan (CN); Qiang Wang, Sichuan (CN); Jianhong Fu, Sichuan (CN)

(73) Assignee: SOUTHWEST PETROLEUM UNIVERSITY, Sichuan (CN)

( * ) Notice: Subject to any disclaimer, the term of this patent is extended or adjusted under 35 U.S.C. 154(b) by 94 days.

(21) Appl. No.: 16/604,518

(22) PCT Filed: Nov. 26, 2018

(86) PCT No.: PCT/CN2018/117456
§ 371 (c)(1),
(2) Date: Oct. 10, 2019

(87) PCT Pub. No.: WO2019/227881
PCT Pub. Date: Dec. 5, 2019

(65) Prior Publication Data
US 2020/0300746 A1    Sep. 24, 2020

(30) Foreign Application Priority Data
May 31, 2018    (CN) .......................... 201810551836.9

(51) Int. Cl.
*G01N 15/08*    (2006.01)
*G01N 33/24*    (2006.01)
(Continued)

(52) U.S. Cl.
CPC ......... *G01N 15/0826* (2013.01); *G01N 33/24* (2013.01); *E21B 49/02* (2013.01)

(58) Field of Classification Search
CPC .... G01N 15/00; G01N 15/08; G01N 15/0826; G01N 33/24; E21B 49/00; E21B 49/02
See application file for complete search history.

(56) References Cited

U.S. PATENT DOCUMENTS

| 9,790,743 B2 * | 10/2017 | Li ......................... E21B 47/007 |
| 10,845,354 B2 * | 11/2020 | Hugghins .......... G01N 15/0826 |
| 2007/0062273 A1 | 3/2007 | Kalfayan |

FOREIGN PATENT DOCUMENTS

| CN | 201963295 U | * 9/2011 | ............. E21B 49/00 |
| CN | 102691497 A | 9/2012 | |

(Continued)

*Primary Examiner* — Nguyen Q. Ha
(74) *Attorney, Agent, or Firm* — Muncy, Geissler, Olds & Lowe, P.C.

(57) ABSTRACT

A physical simulation and calibration device and method for formation pressure testing. The device has a rock core arranged in a rock core clamper, a confining pressure simulation module, formation pressure simulation module, annular pressure simulation module, suction system, thrust force simulation module and drive control system. The thrust force simulation module has a thrust rod which penetrates through a cavity wall on one side of the clamper. The front end of the thrust rod has a simulation probe. The suction system is connected to the thrust rod. The confining pressure simulation module, formation pressure simulation module, annular pressure simulation module, thrust force simulation module and suction system are all connected with the drive control system. The device and method simulate a physical environment of formation pressure testing to achieve physical simulation of formation pressure testing. A formation pressure tester can be corrected and calibrated.

10 Claims, 3 Drawing Sheets

(51) Int. Cl.
    *E21B 49/00*   (2006.01)
    *E21B 49/02*   (2006.01)

(56)         References Cited

FOREIGN PATENT DOCUMENTS

| CN | 103075147 | A | * | 5/2013 | ............ | E21B 47/06 |
| CN | 103233725 | A | | 8/2013 | | |
| CN | 105464649 | A | | 4/2016 | | |
| CN | 106593414 | A | | 4/2017 | | |
| CN | 107201899 | A | * | 9/2017 | ............ | E21B 49/00 |
| CN | 107762482 | A | | 3/2018 | | |
| CN | 108505993 | A | | 9/2018 | | |

* cited by examiner

PHYSICAL SIMULATION AND CALIBRATION DEVICE AND METHOD FOR FORMATION PRESSURE TESTING

TECHNICAL FIELD

The present invention relates to the technical field of instruments for measuring a formation pressure while drilling in the field of oil and gas resource exploration and development, in particular to a physical simulation and calibration device and method for formation pressure testing.

BACKGROUND

The formation pressure refers to the pressure of fluid (oil, gas, water) in pores of a formation, also known as reservoir pressure. For deep exploration, oil and gas exploration, geothermal development, $CO_2$ geological sequestration, nuclear waste geological disposal and other projects involving deep well drilling, formation pressure is one of the important basic parameters. It is of great significance to accurately predict and detect formation pressure. The formation pressure generally increases linearly with depth. If the formation pressure increases by a hydrostatic pressure gradient, it is normal pressure. If the formation pressure is lower than a normal pressure gradient, it is abnormal low pressure. If the formation pressure is higher than the normal pressure gradient, it is abnormal high pressure. Abnormal formation pressure brings a series of challenges to drilling engineering, oil and gas exploitation, geothermal development, $CO_2$ geological sequestration, and nuclear waste geological disposal. If the abnormal formation pressure cannot be accurately predicted and detected, it will cause complicated engineering and serious economic losses and casualties, resulting in very serious consequences.

Conventional formation pressure acquisition methods mainly include a seismic wave method, a drilling rate method, a logging method and a formation testing method. However, conventional formation pressure acquisition methods often have many problems such as low precision and time lag. With the continuous application and development of cable formation testing technology and new demands for drilling engineering, in the mid-to-late 1990s, the concept of formation pressure testing while drilling is proposed in conjunction with the technology for measurement while drilling. A tester is installed in a bottom hole drill assembly to test a formation pressure during the suspension of the drilling operation. In order to solve this problem, Halliburton developed a probe-structured formation WD (while drilling) tester (Geo-Tap system), based on a cable formation tester. Subsequently, foreign oilfield service companies have developed testers with similar probe structures, such as Tes-Trak system in Backer Hughes, Stetho-Scope system in Schlumberger, and Compact-MFT system in Weatherford. The formation pressure testing while drilling is used to test the formation pressure during the drilling process, which effectively solves a series of problems such as long time, high cost, high risk and time lag. In recent years, the development of formation pressure WD (while drilling) testers has been actively developed in China. However, the formation pressure WD testers are mainly monopolized by foreign large-scale oilfield service companies, and there is no fully-developed formation pressure tester with independent intellectual property rights in China. The SDC-I type formation pressure WD tester developed in China is relatively mature, but there are still many problems in stability and reliability. Further researches on relevant physical simulation, testing techniques and testing tools are urgently needed.

The basic principle of formation pressure testing while drilling is as follows: a testing probe is installed on the sidewall of a testing tool, and is pressed against a well wall formation; formation fluid is pumped by a suction system to produce a pressure drop, and a change curve of pressure of a pre-testing chamber with time is recorded by a pressure gauge; when the time is long enough, the formation pressure near the testing probe is restored to the original formation pressure. During the process of testing the formation pressure while drilling, the pressure dynamic response of the pre-testing chamber of the suction system is very critical. The testing pressure responses can be approximately divided into five stages: before testing (a), probe pressing (b), pressure drop (c), pressure recovery (d), and after testing (e). Since Long-term pressure recovery testing is unavailable due to formation pressure testing while drilling, dynamic parameters of the formation, such as formation pressure, permeability, fluid fluidity, and formation damage, must be calculated according to a test pressure response curve. In this case, the relationship between pressure drop (c) and pressure recovery (d) is crucial, directly affecting the testing accuracy of parameters such as formation pressure. In order to accurately calculate or calibrate the dynamic parameters such as formation pressure during the formation pressure testing while drilling, a physical simulation experiment is an important means. However, there are still few physical simulation experiments and calibration studies for formation pressure testing. Existing experimental devices are not accurate enough to interpret and calibrate other dynamic parameters such as formation permeability and fluidity, which mainly results from insufficient accuracy of formation pressure, confining pressure and wellbore pressure control of existing experimental devices, and no physical model experimental device under high formation pressure is reported. Therefore, it is necessary to design and develop a physical simulation and calibration servo control device for high-pressure and high-precision formation pressure testing to improve the design, verification and development capabilities and levels of formation pressure testing, and to accelerate the research and development process of a formation pressure WD tester in China.

SUMMARY

In order to solve the above problems, the present invention provides a physical simulation and calibration device and method for formation pressure testing. The device which uses five hydraulic servo control schemes to control and simulate a confining pressure, a formation pressure and an annular pressure and test a thrust force of a probe, can simulate a physical environment of formation pressure testing and a formation fluid suction testing process to achieve the physical simulation of formation pressure testing, and implement calibration of parameters, such as the formation pressure, formation fluidity, formation permeability and instrument parameters through data interpretation and analysis.

In order to fulfill said objective, the present invention adopts the following technical solution: a physical simulation and calibration device for formation pressure testing comprises an external casing frame, servo motors for providing power and a rock core as a testing target.

The device comprises a rock core clamper disposed on the casing frame; the rock core is disposed inside the rock core clamper; an annular gap is reserved between the rock core and the rock core clamper, and is partitioned by a sealing gasket into a confining pressure chamber located on the circumferential side of the rock core, and a formation pressure chamber and an annular pressure chamber located at the front and rear ends of the rock core; the chamber walls of the rock core clamper, which correspond to the confining pressure chamber, the formation pressure chamber and the annular pressure chamber, are provided with a confining pressure injection hole, a formation pressure injection hole and an annular pressure injection hole respectively; input ends of the confining pressure injection hole, the formation pressure injection hole and the annular pressure injection hole are respectively connected to a confining pressure simulation module, a formation pressure simulation module and an annular pressure simulation module respectively.

The device further comprises a thrust force simulation module on which a thrust rod is disposed, wherein the thrust rod penetrates through the wall on one side of the rock core clamper and is sealed by a sealing gasket; a simulation probe is disposed at the front end of the thrust rod; an annular gap is reserved between the simulation probe and the chamber wall of the rock core clamper.

The device further comprises a suction system which is connected with the thrust rod.

The device further comprises a drive control system to which the confining pressure simulation module, the formation pressure simulation module, the annular pressure simulation module, the push force simulation module and the suction system are all connected.

Further, the confining pressure simulation module comprises a first servo motor; one end of the first servo motor is connected to the drive control system, and the other end is connected to a first speed reducer, a first ball screw, a first hydraulic cylinder, a first group of high pressure stop valves B and a first safety valve in sequence and is finally connected to the confining pressure injection hole; the confining pressure simulation module further comprises an oil tank filled with hydraulic oil; the oil tank is disposed between the first hydraulic cylinder and the first group of high pressure stop valves B; a first group of high pressure stop valves A is also disposed on a pipeline connected to the oil tank; a first pressure sensor is disposed on the first hydraulic cylinder and configured to acquire a confining pressure signal and feeds the confining pressure signal back to the drive control system.

Further, the formation pressure simulation module comprises a second servo motor; one end of the second servo motor is connected to the drive control system, and the other end is connected to a second speed reducer, a second ball screw, a second hydraulic cylinder, a second group of high pressure stop valves B and a second safety valve in sequence and is finally connected to the formation pressure injection hole; the formation pressure simulation module further comprises a second container filled with simulation formation fluid; the second container is disposed between the second hydraulic cylinder and the second group of high pressure stop valves B; a second group of high pressure stop valves A is also disposed on a pipeline connected to the second container; a second pressure sensor is disposed on the second hydraulic cylinder and configured to acquire a formation pressure signal and feeds the formation pressure signal back to the drive control system.

Further, the annular pressure simulation module comprises a third servo motor; one end of the third servo motor is connected to the drive control system, and the other end is connected to a third speed reducer, a third ball screw, a third hydraulic cylinder, a third group of high pressure stop valves B and a third safety valve in sequence and is finally connected to the annular pressure injection hole; the annular pressure simulation module further comprises a third container filled with simulation drilling fluid; the third container is disposed between the third hydraulic cylinder and the third group of high pressure stop valves B; a third group of high pressure stop valves A is also disposed on a pipeline connected to the third container; a third pressure sensor is disposed on the third hydraulic cylinder and configured to acquire an annular pressure signal and feeds the annular pressure signal back to the drive control system.

Further, the thrust force simulation module further comprises a fourth servo motor; one end of the fourth servo motor is connected to the drive control system, and the other end is connected to a fourth speed reducer, a fourth ball screw and a fourth hydraulic cylinder in sequence; the fourth hydraulic cylinder is connected to the thrust rod, and a force sensor is disposed between the fourth hydraulic cylinder and the thrust rod; the force sensor acquires a thrust force signal and feeds the thrust force signal to the drive control system.

Further, the suction system comprises a fifth servo motor; one end of the fifth servo motor is connected to the drive control system, and the other end is connected to a fifth speed reducer, a fifth ball screw, a fifth hydraulic cylinder, and a fifth high pressure stop valve in sequence and is finally connected to the thrust rod through a pipeline; a fifth pressure sensor is disposed on the fifth hydraulic cylinder and configured to acquire a suction signal and feed the suction signal back to the drive control system.

Preferably, an external suction system interface is further disposed on a pipeline connecting the suction system and the thrust rod and is connected to an external suction system; a sixth high pressure stop valve is disposed at the front end of the external suction system interface.

Further, the outer side of the rock core is wrapped with a rubber sleeve.

A simulation and calibration method for the device of the present invention comprises the following steps:

S1, a preparation stage: preparing the rock core according to experimental requirements, and preparing simulation fluid;

S2, installing the rock core: closing all the high pressure stop valves B, dismantling the rock core clamper, replacing the rock core and a sealing gasket of a simulation probe manually, and then installing the rock core clamper;

S3, injecting simulation fluid: closing all the high pressure stop valves A, and injecting hydraulic oil, simulation formation fluid and simulation drilling fluid into the oil tank, the second container and the third container, respectively; turning on a system power supply, opening all high-pressure stop valves A, controlling the corresponding servo motor to drive the corresponding speed reducer and ball screw through the drive control system respectively, so as to drive a piston in the corresponding hydraulic cylinder to suck the corresponding simulation fluid into the hydraulic cylinder;

S4, applying a physical simulation ambient pressure: closing all high pressure stop valves A, opening all high pressure stop valves B, and closing the fifth high pressure stop valve and the sixth high pressure stop valve; first, controlling the first servo motor by the drive control system to drive the first speed reducer and the first ball screw to drive a piston in the first hydraulic cylinder to push hydraulic oil under a confining pressure into the rock core clamper, thereby achieving the application of the confining pressure; then, controlling the second servo motor and the third servo motor by the drive control system to drive the second speed reducer, the third speed reducer, the second ball screw, and the third ball screw to drive pistons in the second hydraulic cylinder and the third hydraulic cylinder to push simulation fluid under a formation pressure and an annular pressure into the rock core clamper, thereby achieving the application of the formation pressure and the annular pressure; simulating a physical environment of formation rock during the formation pressure testing process by applying the confining pressure, the formation pressure and the annular pressure, wherein the confining pressure, the formation pressure and the annular pressure are automatically controlled by a computer;

S5, setting the probe, opening the fifth high pressure stop valve or the sixth high pressure stop valve; then, controlling the fourth servo motor by the drive control system to drive the fourth speed reducer and the fourth ball screw, so as to drive the force sensor and the thrust rod, such that the simulation probe is set on the right end surface of the rock core, wherein a thrust force and a pushing displacement are automatically controlled by a computer;

S6, starting a pumping sequence: controlling the fifth servo motor by the drive control system to drive the fifth speed reducer and the fifth ball screw to drive a piston in the fifth hydraulic cylinder to suck simulation formation fluid from the rock core, the simulation formation fluid entering the fifth hydraulic cylinder through the simulation probe, the thrust rod and the high pressure stop valve, and continuing to wait for pressure recovery after the suction is completed, and the fifth pressure sensor recording a pressure response during the suction testing process; if the pressure is subjected to multiple step-by-step suction testing, repeating step S6;

S7, testing end sequence: controlling the corresponding servo motor by the drive control system to drive the corresponding speed reducer and ball screw, so as to drive a piston in the corresponding hydraulic cylinder to retract to release the confining pressure, the formation pressure and the annular pressure; controlling the fourth servo motor by the drive control system to drive the fourth speed reducer and the fourth ball screw, so as to drive the force sensor, the thrust rod and the simulation probe to release from the right end surface of the rock core; controlling the fifth servo motor by the drive control system to drive the fifth speed reducer and the fifth ball screw, so as to drive a piston in the fifth hydraulic cylinder to discharge formation fluid; and S8, ending the testing: closing all high pressure stop valves B and opening all high pressure stop valves A, and controlling the corresponding servo motor by the drive control system to drive the corresponding speed reducer and ball screw, so as to drive a piston in a corresponding hydraulic cylinder to discharge the corresponding simulation fluid; turning off the power supply, dismantling the rock core clamper, manually removing the rock core and a sealing gasket of the simulation probe, installing the rock core clamper and tidying an experimental platform.

It should be noted that if an external suction system is used in step S6, the operation steps are as follows: controlling the external suction system by the external drive control system to suck simulation formation fluid, the simulation formation fluid entering a hydraulic cylinder of the suction system through the simulation probe, the thrust rod and the high pressure stop valve, and continuing to wait for pressure recovery after the suction is completed, and a system pressure sensor recording a pressure response during the suction testing process; if the pressure is subjected to multiple step-by-step suction testing, repeating step S6;

with respect to step S7, if the external suction system is adopted, controlling the suction system by the external drive control system to discharge simulation formation fluid, and if the pressure is subjected to multiple step-by-step suction testing, repeating steps S6 and S7.

Compared with the prior art, the present invention has the beneficial effects: a physical environment of formation pressure testing and a formation fluid suction testing process can be simulated to achieve physical simulation of formation pressure testing, a formation pressure tester can be corrected and calibrated, and the formation pressure testing ability and control precision are improved; the levels of design, verification and development capabilities of the formation pressure testing in China can be promoted, and the research and development process of a formation pressure tester in China can be accelerated.

in drawings, reference symbols present the following components: 1—drive control system; 21—first servo motor; 22—second servo motor; 23—third servo motor; 24—fourth servo motor; 25—fifth servo motor; 31—first speed reducer; 32—second speed reducer; 33—third speed reducer; 34—fourth speed reducer; 35—fifth speed reducer; 41—first ball screw; 42—second ball screw; 43—third ball screw; 44—fourth ball screw; 45—fifth ball screw; 51—first hydraulic cylinder; 52—second hydraulic cylinder; 53—third hydraulic cylinder; 55—fifth hydraulic cylinder; 61—first pressure sensor; 62—second pressure sensor; 63—third pressure sensor; 65—fifth pressure sensor; 71—first group of high pressure stop valves A; 72—second group of high pressure stop valves A; 73—third group of high pressure stop valves A; 81—first group of high pressure stop valves B; 82—second group of high pressure stop valves B; 83—third group of high pressure stop valves B; 91—oil tank; 92—second container; 93—third container; 10—rock core clamper; 11—force sensor; 12—thrust rod; 13—simulation probe; 14—rock core; 151—first safety valve; 152—second safety valve; 153—third safety valve; 16—fifth high pressure stop valve; 17—sixth high pressure stop valve.

DETAILED DESCRIPTION

For a better understanding of the technical features, the objectives and the effects of the present invention, the specific embodiments of the present invention will be described with reference to the accompanying drawings, but the protection scope of the present invention is not limited to the followings.

Figure 1:
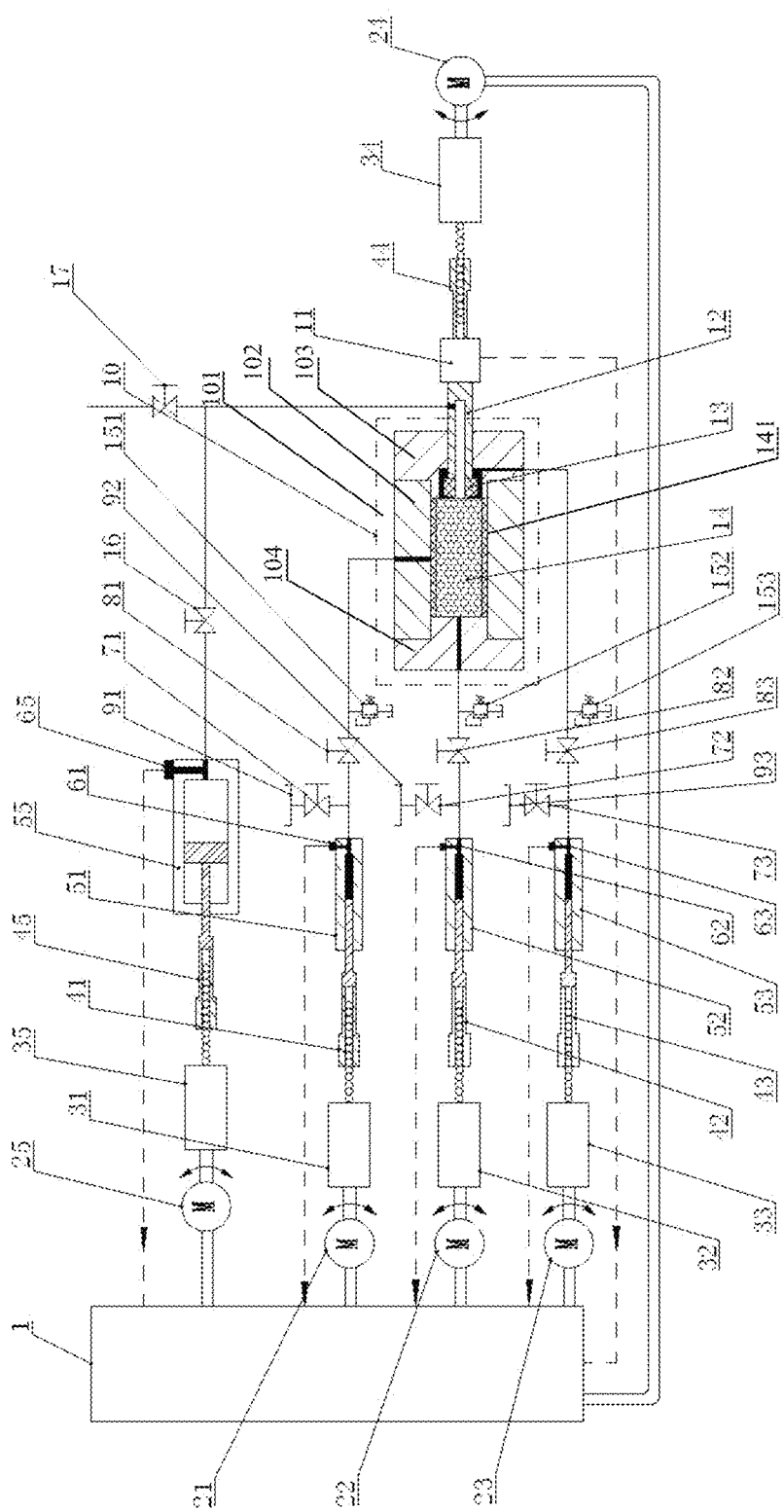
FIG. 1 is a schematic diagram showing a structure of the present invention.

As shown in FIG. 1, a physical simulation and calibration device for formation pressure testing comprises an external casing frame, servo motors for supplying power, and a rock core as a testing target.

The device comprises a rock core clamper 10 disposed on the casing frame; the rock core 14 is disposed inside the rock core clamper 10; an annular gap 101 is reserved between the rock core 14 and the rock core clamper 10, and is partitioned by a sealing gasket into a confining pressure chamber 102 located on the circumferential side of the rock core 14, and a formation pressure chamber 103 and an annular pressure chamber 104 located at the front and rear ends of the rock core 14; the chamber walls of the rock core clamper 10, which correspond to the confining pressure chamber 102, the formation pressure chamber 103 and the annular pressure chamber 104, are provided with a confining pressure injection hole, a formation pressure injection hole and an annular pressure injection hole respectively; input ends of the confining pressure injection hole, the formation pressure injection hole and the annular pressure injection hole are respectively connected to a confining pressure simulation module, a formation pressure simulation module and an annular pressure simulation module respectively.

The device further comprises a thrust force simulation module on which a thrust rod 12 is disposed, wherein the thrust rod 12 penetrates through the wall on one side of the rock core clamper 10 and is sealed by a sealing gasket; a simulation probe 13 is disposed at the front end of the thrust rod 12; an annular gap is reserved between the simulation probe 13 and the chamber wall of the rock core clamper 10.

The device further comprises a suction system which is connected with the thrust rod 12.

The device further comprises a drive control system 1 to which the confining pressure simulation module, the formation pressure simulation module, the annular pressure simulation module, the push force simulation module and the suction system are all connected.

The confining pressure simulation module comprises a first servo motor 21; one end of the first servo motor 21 is connected to the drive control system 1, and the other end is connected to a first speed reducer 31, a first ball screw 41, a first hydraulic cylinder 51, a first group of high pressure stop valves B 81 and a first safety valve 151 in sequence and is finally connected to the confining pressure injection hole; the confining pressure simulation module further comprises an oil tank 91 filled with hydraulic oil; the oil tank 91 is disposed between the first hydraulic cylinder 51 and the first group of high pressure stop valves B 81; a first group of high pressure stop valves A 71 is also disposed on a pipeline connected to the oil tank 91; a first pressure sensor 61 is disposed on the first hydraulic cylinder 51 and configured to acquire a confining pressure signal and feeds the confining pressure signal back to the drive control system 1.

The formation pressure simulation module comprises a second servo motor 22; one end of the second servo motor 22 is connected to the drive control system 1, and the other end is connected to a second speed reducer 32, a second ball screw 42, a second hydraulic cylinder 52, a second group of high pressure stop valves B 82 and a second safety valve 152 in sequence and is finally connected to the formation pressure injection hole; the formation pressure simulation module further comprises a second container 92 filled with simulation formation fluid; the second container 92 is disposed between the second hydraulic cylinder 52 and the second group of high pressure stop valves B 82; a second group of high pressure stop valves A 72 is also disposed on a pipeline connected to the second container 92; a second pressure sensor 62 is disposed on the second hydraulic cylinder 52 and configured to acquire a formation pressure signal and feeds the formation pressure signal back to the drive control system 1.

The annular pressure simulation module comprises a third servo motor 23; one end of the third servo motor 23 is connected to the drive control system 1, and the other end is connected to a third speed reducer 33, a third ball screw 43, a third hydraulic cylinder 53, a third group of high pressure stop valves B 83 and a third safety valve 153 in sequence and is finally connected to the annular pressure injection hole; the annular pressure simulation module further comprises a third container 93 filled with simulation drilling fluid; the third container 93 is disposed between the third hydraulic cylinder 53 and the third group of high pressure stop valves B 83; a third group of high pressure stop valves A 73 is also disposed on a pipeline connected to the third container 93; a third pressure sensor 63 is disposed on the third hydraulic cylinder 53 and configured to acquire an annular pressure signal and feeds the annular pressure signal back to the drive control system 1.

The thrust force simulation module further comprises a fourth servo motor 24; one end of the fourth servo motor 24 is connected to the drive control system 1, and the other end is connected to a fourth speed reducer 34, a fourth ball screw 44 and a fourth hydraulic cylinder 54 in sequence; the fourth hydraulic cylinder 54 is connected to the thrust rod 12, and a force sensor 11 is disposed between the fourth hydraulic cylinder 54 and the thrust rod 12; the force sensor 11 acquires a thrust force signal and feeds the thrust force signal to the drive control system 1.

The suction system comprises a fifth servo motor 25; one end of the fifth servo motor 25 is connected to the drive control system 1, and the other end is connected to a fifth speed reducer 35, a fifth ball screw 45, a fifth hydraulic cylinder 55, and a fifth high pressure stop valve 16 in sequence and is finally connected to the thrust rod 12 through a pipeline; a fifth pressure sensor 65 is disposed on the fifth hydraulic cylinder 55 and configured to acquire a suction signal and feed the suction signal back to the drive control system 1.

An external suction system interface is further disposed on a connection pipeline between the suction system and the thrust rod 12 and is connected to an external suction system; a sixth high pressure stop valve 17 is disposed at the front end of the external suction system interface.

The outer side of the rock core 14 is wrapped with a rubber sleeve 141.

Figure 2:
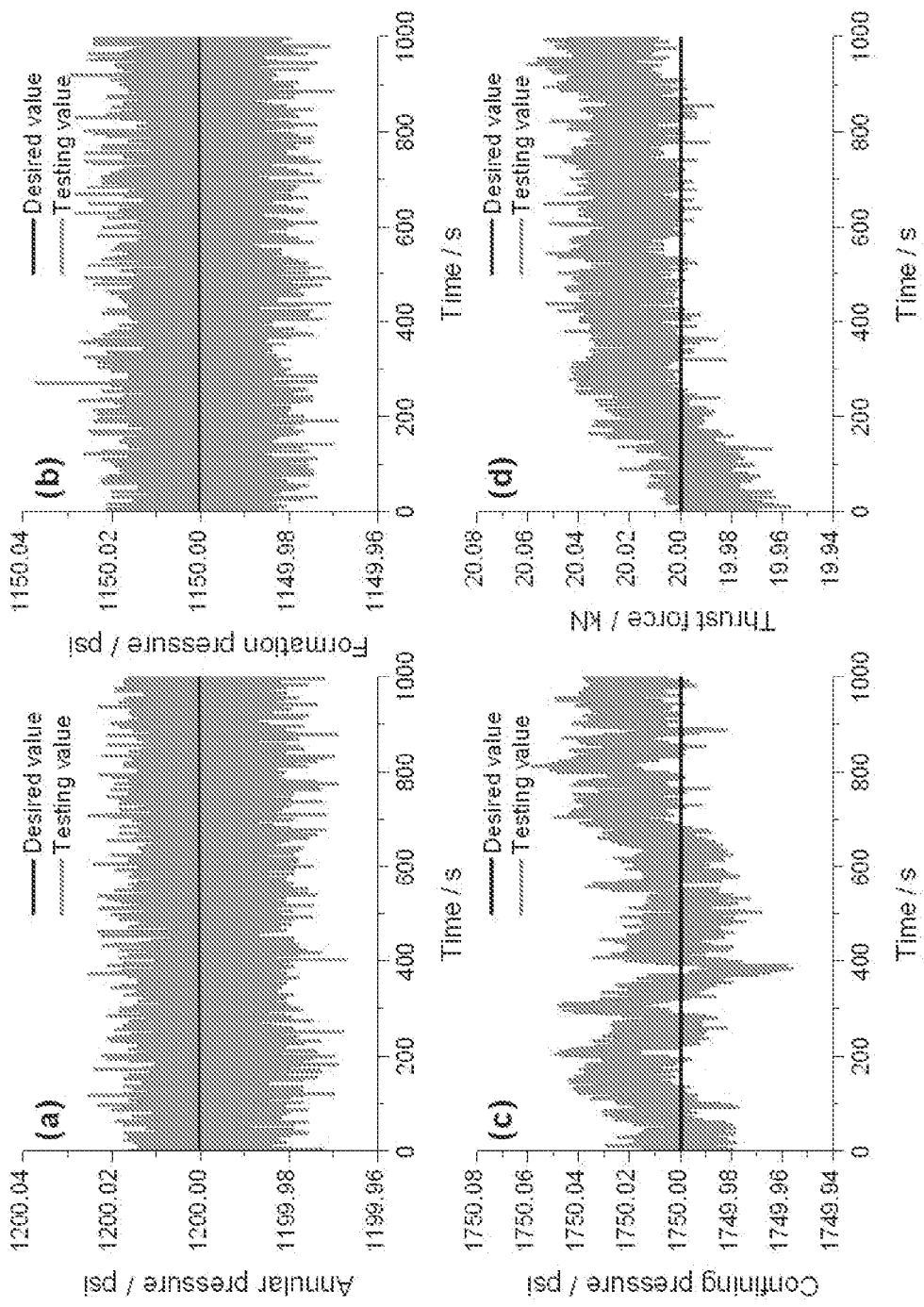
FIG. 2 is a parameter control precision monitoring diagram of a system of the present invention.
Figure 3:
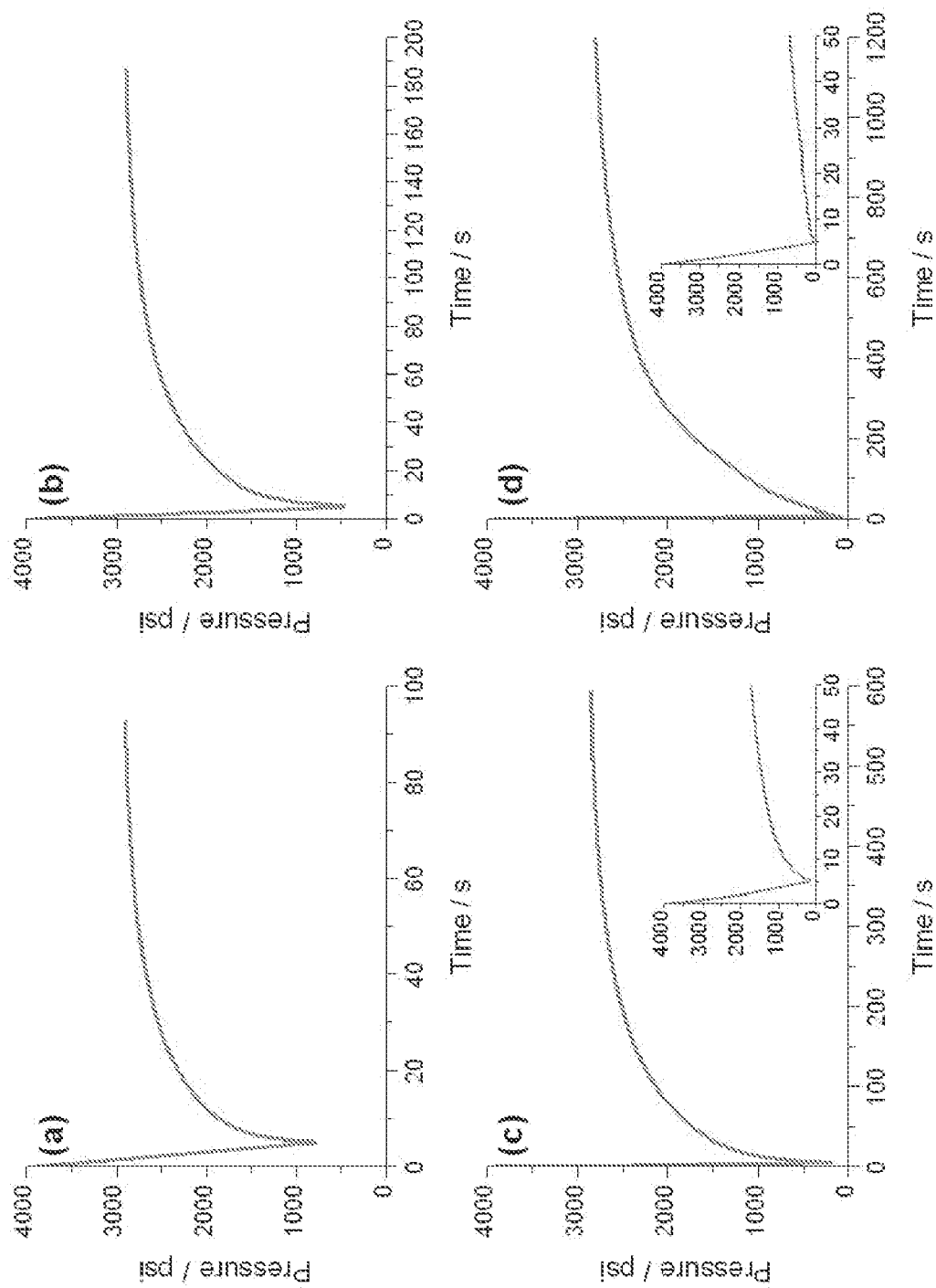
FIG. 3 is a corresponding pressure graph during formation pressure testing of the present invention.

As shown in FIG. 1 to FIG. 3, a simulation and calibration method for the device of the present invention comprises the following steps:

S1, a preparation stage: preparing the rock core 14 according to experimental requirements, and preparing simulation fluid;

S2, installing the rock core 14: closing all the high pressure stop valves B, dismantling the rock core clamper 10, replacing the rock core 14 and a sealing gasket of a simulation probe 13 manually, and then installing the rock core clamper 10;

S3, injecting simulation fluid: closing all the high pressure stop valves A, and injecting hydraulic oil, simulation formation fluid and simulation drilling fluid into the oil tank 91, the second container 92 and the third container 93, respectively; turning on a system power supply, opening all high-pressure stop valves A, controlling the corresponding servo motor to drive the corresponding reducer and ball screw through the drive control system 1 respectively, so as to drive a piston in the corresponding hydraulic cylinder to suck the corresponding simulation fluid into the hydraulic cylinder;

S4, applying a physical simulation ambient pressure: closing all high pressure stop valves A, opening all high pressure stop valves B, and closing the fifth high pressure stop valve 16 and the sixth high pressure stop valve 17; first, controlling the first servo motor 21 by the drive control system 1 to drive the first speed reducer 31 and the first ball screw 41 to drive a piston in the first hydraulic cylinder 51 to push hydraulic oil under a confining pressure into the rock core clamper 10, thereby achieving the application of the confining pressure; then, controlling the second servo motor 22 and the third servo motor 23 by the drive control system 1 to drive the second speed reducer 32, the third speed reducer 33, the second ball screw 42 and the third ball screw 43 to drive pistons in the second hydraulic cylinder 52 and the third hydraulic cylinder 53 to push simulation fluid under a formation pressure and an annular pressure into the rock core clamper 10, thereby achieving the application of the formation pressure and the annular pressure; simulating a physical environment of formation rock during the formation pressure testing process by applying the confining pressure, the formation pressure and the annular pressure, wherein the confining pressure, the formation pressure and the annular pressure are automatically controlled by a computer;

S5, setting the probe: opening the fifth high pressure stop valve 16 or the sixth high pressure stop valve 17; then, controlling the fourth servo motor 24 by the drive control system 1 to drive the fourth speed reducer 34 and the fourth ball screw 44, so as to drive the force sensor 11 and the thrust rod 12, such that the simulation probe 13 is set on the right end surface of the rock core 14, wherein a thrust force and a pushing displacement are automatically controlled by a computer;

S6, starting a pumping sequence: controlling the fifth servo motor 25 by the drive control system 1 to drive the fifth speed reducer 35 and the fifth ball screw 45 to drive a piston in the fifth hydraulic cylinder 55 to suck simulation formation fluid from the rock core 14, the simulation formation fluid entering the fifth hydraulic cylinder 55 through the simulation probe 13, the thrust rod 12 and the high pressure stop valve 16, and continuing to wait for pressure recovery after the suction is completed, and the fifth pressure sensor 65 recording a pressure response during the suction testing process; if the pressure is subjected to multiple step-by-step suction testing, repeating step S6;

S7, testing end sequence: controlling the corresponding servo motor by the drive control system 1 to drive the corresponding speed reducer and ball screw, so as to drive a piston in the corresponding hydraulic cylinder to retract to release the confining pressure, the formation pressure and the annular pressure; controlling the fourth servo motor 24 by the drive control system 1 to drive the fourth speed reducer 34 and the fourth ball screw 44, so as to drive the force sensor 11, the thrust rod 12 and the simulation probe 13 to release from the right end surface of the rock core 14; controlling the fifth servo motor 25 by the drive control system 1 to drive the fifth speed reducer 35 and the fifth ball screw 45, so as to drive a piston in the fifth hydraulic cylinder 55 to discharge formation fluid; and S8, ending the testing: closing all high pressure stop valves B and opening all high pressure stop valves A, and controlling the corresponding servo motor by the drive control system 1 to drive the corresponding speed reducer and ball screw, so as to drive a piston in a corresponding hydraulic cylinder to discharge the corresponding simulation fluid; turning off the power supply, dismantling the rock core clamper 10, manually removing the rock core 14 and a sealing gasket of the simulation probe 13, installing the rock core clamper 14 and tidying an experimental platform.

It should be noted that if an external suction system is used in step S6, the operation steps are as follows: controlling the external suction system by the external drive control system to suck simulation formation fluid, the simulation formation fluid entering a hydraulic cylinder of the suction system through the simulation probe 13, the thrust rod 12 and the high pressure stop valve 17, and continuing to wait for pressure recovery after the suction is completed, and a system pressure sensor recording a pressure response during the suction testing process; if the pressure is subjected to multiple step-by-step suction testing, repeating step S6;

with respect to step S7, if the external suction system is adopted, controlling the suction system by the external drive control system to discharge simulation formation fluid, and if the pressure is subjected to multiple step-by-step suction testing, repeating steps S6 and S7.

The control precision of the device of the present invention for each piece of set data is as follows: (1) confining pressure control accuracy, 10 Psi; (2) formation pressure control accuracy, 10 Psi; (3) annular pressure control accuracy, 10 Psi; (4) probe thrust force control accuracy, 200N.

As shown in FIG. 2, the monitoring results of the annular pressure, formation pressure, confining pressure and thrust force in 1000 s are given. The control objectives for the annular pressure, formation pressure, confining pressure and thrust force are 1200 psi, 1150 psi, 1750 psi, 20 kN, respectively. Corresponding control fluctuations are approximately 0.07 psi, 0.08 psi, 0.11 psi, and 0.11 kN, all of which meet the control accuracy under design. The pressure control accuracy is ±1.0 psi and the thrust force control accuracy is ±1.0%.

As shown in FIG. 3, four typical sandstone testing results are given. The testing parameters and results are shown in Table 1 below. It is not difficult to find that the errors of formation pressure testing and interpretation results is within 1.0% respectively, and the maximum error is only −0.92%, indicating that the accuracy of the system meets the design requirements.

| Serial No. | Parameters | Sample 1 | Sample 2 | Sample 3 | Sample 4 |
|---|---|---|---|---|---|
| 1. | Lithology | Coarse silt | Coarse silt | Fine silt | Fine silt |
| 2. | Permeability/mD | 203.5 | 105.2 | 50.8 | 10.2 |
| 3. | Confining pressure/psi | 4500 | 4500 | 4500 | 4500 |
| 4. | Annular pressure/psi | 3900 | 3900 | 3900 | 3900 |
| 5. | Formation pressure/psi | 3000 | 3000 | 3000 | 3000 |
| 6. | Pressure suction time $t_0$/s | 5.0 | 5.0 | 5.0 | 5.0 |
| 7. | Suction rate $q_0$/(ml/s) | 3.0 | 1.5 | 1.0 | 0.5 |
| 8. | Minimum pressure/psi | 788 | 467 | 200 | 50 |
| 9. | Pressure drop/psi | 3112 | 3433 | 3700 | 3850 |
| 10. | Ultimate recovery pressure/psi | 2904 | 2898 | 2858 | 2827 |
| 11. | Pressure recovery/psi | 2116 | 2431 | 2658 | 2777 |
| 12. | Pressure drop time $t1$/s | 90 | 185 | 550 | 1300 |

-continued

| Serial No. | Parameters | Sample 1 | Sample 2 | Sample 3 | Sample 4 |
|---|---|---|---|---|---|
| 13. | Formation pressure interpretation result/psi | 2903.12 | 2895.12 | 2880.50 | 2873.22 |
| 14. | Absolute error/psi | 3.12 | −4.88 | −19.50 | −26.78 |
| 15. | Relative error/% | 0.11 | −0.17 | −0.67 | −0.92 |

The above disclosure only refers to the preferred embodiments of the present invention, and is of course not intended to limit the scope of the present invention. Therefore, equivalent changes made in accordance with the claims of the present invention are still within the scope of the present invention.

The invention claimed is:

1. A physical simulation and calibration device for formation pressure testing, comprising an servo motors for supplying power, and a rock core as a testing target, wherein the device comprises a rock core clamper;
the rock core is disposed inside the rock core clamper;
an annular gap is reserved between the rock core clamper inner walls and the rock core, and is partitioned into a confining pressure chamber located in the reserved annular gap between the rock core clamper inner walls and outer circumference of the rock core, a formation pressure chamber located between the rock core clamper inner walls and a front end of the rock core, and an annular pressure chamber located between the rock core clamper inner walls and a rear end of the rock core opposite to the front end;
the confining pressure chamber, the formation pressure chamber and the annular pressure chamber, each are provided with a confining pressure injection hole, a formation pressure injection hole and an annular pressure injection hole respectively; input ends of the confining pressure injection hole, the formation pressure injection hole and the annular pressure injection hole are respectively connected to a confining pressure simulation module, a formation pressure simulation module and an annular pressure simulation module respectively;
the device further comprises a thrust force simulation module on which a thrust rod is disposed, wherein the thrust rod penetrates through a wall of the rock core clamper facing the rear end of the rock core; a simulation probe is disposed at the penetrating end of the thrust rod;
the device further comprises a suction system which is connected with the thrust rod;
the device further comprises a drive control system to which the confining pressure simulation module, the formation pressure simulation module, the annular pressure simulation module, the push force simulation module and the suction system are all connected.

2. The physical simulation and calibration device for formation pressure testing according to claim 1, wherein the outer side of the rock core is wrapped with a rubber sleeve.

3. The physical simulation and calibration device for formation pressure testing according to claim 1, wherein the confining pressure simulation module comprises a first servo motor; one end of the first servo motor is connected to the drive control system, and the other end is connected to a first speed reducer, a first ball screw, a first hydraulic cylinder, a first group of high pressure stop valves B and a first safety valve in sequence and is finally connected to the confining pressure injection hole; the confining pressure simulation module further comprises an oil tank filled with hydraulic oil; the oil tank is disposed between the first hydraulic cylinder and the first group of high pressure stop valves B; a first group of high pressure stop valves A is also disposed on a pipeline connected to the oil tank; a first pressure sensor is disposed on the first hydraulic cylinder and configured to acquire a confining pressure signal and feeds the confining pressure signal back to the drive control system.

4. The physical simulation and calibration device for formation pressure testing according to claim 3, wherein the formation pressure simulation module comprises a second servo motor; one end of the second servo motor is connected to the drive control system, and the other end is connected to a second speed reducer, a second ball screw, a second hydraulic cylinder, a second group of high pressure stop valves B and a second safety valve in sequence and is finally connected to the formation pressure injection hole; the formation pressure simulation module further comprises a second container filled with simulation formation fluid; the second container is disposed between the second hydraulic cylinder and the second group of high pressure stop valves B; a second group of high pressure stop valves A is also disposed on a pipeline connected to the second container; a second pressure sensor is disposed on the second hydraulic cylinder and configured to acquire a formation pressure signal and feeds the formation pressure signal back to the drive control system.

5. The physical simulation and calibration device for formation pressure testing according to claim 4, wherein the annular pressure simulation module comprises a third servo motor; one end of the third servo motor is connected to the drive control system, and the other end is connected to a third speed reducer, a third ball screw, a third hydraulic cylinder, a third group of high pressure stop valves B and a third safety valve in sequence and is finally connected to the annular pressure injection hole; the annular pressure simulation module further comprises a third container filled with simulation drilling fluid; the third container is disposed between the third hydraulic cylinder and the third group of high pressure stop valves B; a third group of high pressure stop valves A is also disposed on a pipeline connected to the third container; a third pressure sensor is disposed on the third hydraulic cylinder and configured to acquire an annular pressure signal and feeds the annular pressure signal back to the drive control system.

6. The physical simulation and calibration device for formation pressure testing according to claim 5, wherein the thrust force simulation module further comprises a fourth servo motor; one end of the fourth servo motor is connected to the drive control system, and the other end is connected to a fourth speed reducer, and a fourth ball screw the force sensor acquires a thrust force signal and feeds the thrust force signal to the drive control system.

7. The physical simulation and calibration device for formation pressure testing according to claim 6, wherein the suction system comprises a fifth servo motor; one end of the fifth servo motor is connected to the drive control system, and the other end is connected to a fifth speed reducer, a fifth ball screw, a fifth hydraulic cylinder, and a fifth high pressure stop valve in sequence and is finally connected to the thrust rod through a pipeline; a fifth pressure sensor is disposed on the fifth hydraulic cylinder and configured to acquire a suction signal and feed the suction signal back to the drive control system.

8. The physical simulation and calibration device for formation pressure testing according to claim 7, wherein an external suction system interface is further disposed on a pipeline connecting the suction system and the thrust rod and is connected to an external suction system; a sixth high pressure stop valve is disposed at the front end of the external suction system interface.

9. A physical simulation and calibration method for formation pressure testing according to claim 8, comprising the following steps:
S1, a preparation stage: preparing the rock core according to experimental requirements, and preparing simulation fluid;
S2, installing the rock core: closing all the high pressure stop valves B, dismantling the rock core clamper, replacing the rock core manually, and then installing the rock core clamper;
S3, injecting simulation fluid: closing all the high pressure stop valves A, and injecting hydraulic oil, simulation formation fluid and simulation drilling fluid into the oil tank, the second container and the third container, respectively; turning on a system power supply, opening all high-pressure stop valves A, controlling the corresponding servo motor to drive the speed reducer and the ball screw through the drive control system respectively, so as to drive a piston in the hydraulic cylinder to suck the corresponding simulation fluid into the hydraulic cylinder;
S4, applying a physical simulation ambient pressure: closing all high pressure stop valves A, opening all high pressure stop valves B, and closing the fifth high pressure stop valve and the sixth high pressure stop valve; first, controlling the first servo motor by the drive control system to drive the first speed reducer and the first ball screw to drive a piston in the first hydraulic cylinder to push hydraulic oil under a confining pressure into the rock core clamper, thereby achieving the application of the confining pressure; then, controlling the second servo motor and the third servo motor by the drive control system to drive the second speed reducer, the third speed reducer, the second ball screw and the third ball screw to drive pistons in the second hydraulic cylinder and the third hydraulic cylinder to push simulation fluid under a formation pressure and an annular pressure into the rock core clamper, thereby achieving the application of the formation pressure and the annular pressure; simulating a physical environment of formation rock during the formation pressure testing process by applying the confining pressure, the formation pressure and the annular pressure, wherein the confining pressure, the formation pressure and the annular pressure are automatically controlled by a computer;
S5, setting the probe: opening the fifth high pressure stop valve or the sixth high pressure stop valve; then, controlling the fourth servo motor by the drive control system to drive the fourth speed reducer and the fourth ball screw, so as to drive the force sensor and the thrust rod, such that the simulation probe is set on the right end surface of the rock core, wherein a thrust force and a pushing displacement are automatically controlled by a computer;
S6, starting a pumping sequence: controlling the fifth servo motor by the drive control system to drive the fifth speed reducer and the fifth ball screw to drive a piston in the fifth hydraulic cylinder to suck simulation formation fluid from the rock core, the simulation formation fluid entering the fifth hydraulic cylinder through the simulation probe, the thrust rod and the high pressure stop valve, and continuing to wait for pressure recovery after the suction is completed, and the fifth pressure sensor recording a pressure response during the suction testing process; if the pressure is subjected to multiple step-by-step suction testing, repeating step S6;
S7, testing end sequence: controlling the corresponding servo motor by the drive control system to drive the corresponding speed reducer and ball screw, so as to drive a piston in the corresponding hydraulic cylinder to retract to release the confining pressure, formation pressure and annular pressure; controlling the fourth servo motor by the drive control system to drive the fourth speed reducer and the fourth ball screw, so as to drive the force sensor, the thrust rod and the simulation probe to release from the right end surface of the rock core; controlling the fifth servo motor by the drive control system to drive the fifth speed reducer and the fifth ball screw, so as to drive a piston in the fifth hydraulic cylinder to discharge formation fluid; and
S8, ending the testing: closing all high pressure stop valves B and opening all high pressure stop valves A, and controlling the corresponding servo motor by the drive control system to drive the corresponding speed reducer and ball screw, so as to drive a piston in a corresponding hydraulic cylinder to discharge the corresponding simulation fluid; turning off the power supply, dismantling the rock core clamper, manually removing the rock core, installing the rock core clamper and tidying an experimental platform.

10. The physical simulation and calibration method for formation pressure testing according to claim 9, wherein if an external suction system is used in step S6, the operation steps are as follows: controlling the external suction system by the external drive control system to suck simulation formation fluid, the simulation formation fluid entering a hydraulic cylinder of the suction system through the simulation probe, the thrust rod and the high pressure stop valve, and continuing to wait for pressure recovery after the suction is completed, and a system pressure sensor recording a pressure response during the suction testing process; if the pressure is subjected to multiple step-by-step suction testing, repeating step S6; with respect to step S7, if the external suction system is adopted, controlling the suction system by the external drive control system to discharge simulation formation fluid, and if the pressure is subjected to multiple step-by-step suction testing, repeating steps S6 and S7.

* * * * *